United States Patent [19]
Weber et al.

[11] Patent Number: 5,268,749
[45] Date of Patent: Dec. 7, 1993

[54] APPARATUS AND METHOD FOR PROVIDING UNIFORM ILLUMINATION OF A SAMPLE PLANE

[75] Inventors: William L. Weber; Harold Van Aken, both of Wallkill, N.Y.

[73] Assignee: Kollmorgen Corporation, Simsbury, Conn.

[21] Appl. No.: 736,467

[22] Filed: Jul. 26, 1991

[51] Int. Cl.⁵ ............................................ G01N 21/47
[52] U.S. Cl. .................................. 356/446; 356/236; 359/387
[58] Field of Search ................. 356/445, 446, 236; 250/228; 359/387

[56] References Cited

U.S. PATENT DOCUMENTS

| | | | |
|---|---|---|---|
| 4,022,534 | 5/1977 | Kishner | 356/446 |
| 4,076,421 | 2/1978 | Kishner | 356/446 X |
| 4,082,458 | 4/1978 | Fukui et al. | 356/445 X |
| 4,232,971 | 11/1980 | Suga | 356/446 |
| 4,422,135 | 12/1983 | McCamy | 362/346 |
| 4,475,796 | 10/1984 | Kimura | 359/387 |
| 4,687,304 | 8/1987 | Piller et al. | 359/387 |
| 4,865,456 | 9/1989 | Mast et al. | 356/446 |
| 4,881,802 | 11/1989 | Stankewitz | 359/387 |
| 4,892,409 | 1/1990 | Smith | 356/236 X |

FOREIGN PATENT DOCUMENTS

0095759 5/1983 European Pat. Off. .

*Primary Examiner*—Vincent P. McGraw
*Attorney, Agent, or Firm*—Morgan & Finnegan

[57] ABSTRACT

A conical illuminator for use in colorimetry, spectrophotometry, densitometry or sensitometry. In a preferred embodiment, light from a source such as a pulsed xenon lamp is integrated within a integrating chamber. The light source may be placed in a second integrating chamber adjacent to the aforementioned integrating chamber. Alternatively, the lamp may be placed directly within the integrating chamber. The light is emitted through an exit port and conformed to a conical configuration, according to a pre-selected standard, via an annular stop. An imaging optic relays the conformed light uniformly onto a sample plane. The annular stop is placed at or near the tangential focal length of the imaging optic. The annular stop may be coated with a light absorbing coating, or can be formed with a grooved or mirrored surface. Alternatively, in lieu of an integrating chamber, a diffuser may be employed for homogenizing the light. Various configurations of the imaging optic and annular stop are possible.

44 Claims, 4 Drawing Sheets

APPARATUS AND METHOD FOR PROVIDING UNIFORM ILLUMINATION OF A SAMPLE PLANE

FIELD OF THE INVENTION

This invention relates to a sample illuminator, and more particularly, to a sample illuminator for use in colorimetry, spectrophotometry, sensitometry or densitometry.

BACKGROUND

Spectrophotometers are employed to measure diffuse reflectance in many narrow spectral bands, and these devices are employed, for example, in the color measurement of such substances as paints, plastics, textiles, and the analysis of powdered chemicals or biological specimens. The diffuse reflectance factor is defined as the ratio of light flux reflected from a sample (e.g., light efflux), to the light flux incident upon the sample (e.g., light influx), and is compared relative to a "perfect white diffuser". The diffuse reflectance measurement excludes specular reflections.

When visually examining a surface critically in order to judge its color, or to discern an image or a pattern, it is not only important to provide illumination to the surface so that the surface is well illuminated, but it is also important that no light is specularly reflected back to the eye. This can be achieved by viewing the plane surface from the normal, and by illuminating the surface 45° to the normal. See, e.g., American National Standard for Photography (Sensitometry), "Density Measurements-Geometric Conditions for Reflection Density", American National Standards Institute )"ANSI") PH 2.17-1985; Commision Internationale l'Eclairage (CIE) No. 15.2 (1986), "Colorimetry."

Accordingly, a need exists for an illuminator for use in colorimetry, spectrophotometry, densitometry or sensitometry which creates the geometric conditions of 45° illumination for viewing or photographing a sample object.

ANSI has established geometric conditions for reflection density or reflectance factor measurements, such as those contemplated for colorimetry, or which conform to the practical situations normally encountered for viewing reflection-type photographs or graphic reproductions.

For general use in colorimetry or spectrophotometry, ANSI has established an applicable standard for illumination, commonly referred to as the 45°:0° (or 0°:45°) standard of illumination. This standard has been specifically selected in order to illuminate an object surface, whose reflection density is to be measured, at print angles between 40 and 50 degrees to the normal of the object surface. The measurements are typically viewed or taken from the normal to the object surface. This standard has been found to produce conditions which tend to minimize surface glare and maximize the density range of the image.

Under the ANSI standard, a 45° cone of light impinges upon the object, while the cone possesses a $+/-5°$ subtended angle. For example, in 45°:0° illumination, the incident light (or "influx") is concentrated in an annulus that impinges at a central 45° angle to the sample, with a subject angular spread of incident light (or subtended angle) between 40° and 50° to the sample. The diffusely reflected light (or "efflux ") is collected normal to the sample. Although the measured efflux is at its maximum detection sensitivity at the normal, the ANSI standard provides that the measured diffuse light possesses a measured subtense of approximately 10° (i.e., a cone of light defined by a surface 5° from the normal).

As described in ANSI PH 2.17-1985, "Density Measurements-Geometric Conditions For Reflection Density", for the 45°:0° standard, the incoming influx radiance is established to have a maximum at 45° to the normal to the sampling aperture, and shall be negligible at angles less than 40° or more than 50° to the normal at any point on the sampling aperture.

Similarly, for 0°:45° illumination, light incident upon the sample surface would be restricted to an influx cone of light having a 0° central angle, but restricted to a cone having an outside surface 5° from the normal. The measured diffused efflux, having a maximum detection sensitivity at 45° from the normal, ranges in a cone restricted to 40° and 50° from the normal.

It will be appreciated by those skilled in the art that, as reflected in the designation of the ANSI standard (45°:0°, or 0°:45°), the corresponding advantages attendant with the 45° configuration are obtained whether the object is illuminated at 45° and viewed from the normal, or whether the object is illuminated at the normal and viewed from 45°. Thus, it is understood that the concepts disclosed for the apparatus and method disclosed herein may also be used to provide the efflux geometry for a 0°:45° configuration.

Various illuminators are known in the prior art. For example, U.S. Pat. Nos. 4,022,534 and 4,076,421 to Kishner disclose a 45°/0° illuminator/collector geometry. Kishner '534 employs a wedge-shaped diffuser and a non-imaging, cylindrical reflector to obtain 45° illumination, while Kishner '421 employs a diffusing screen with the non-imaging cylindrical reflector to obtain the 45° illumination. The Kishner illuminators, although providing a measure of 45° illumination, suffer in that the illumination at all points along the imaging plane is not uniformly 45°. Uniform 45° is only achieved at the center of the imaging plane due to the non-imaging of the cylindrical reflector. The baffles of Kishner, which can not be telecentric to the cylindrical reflector, are only configured to prevent some passage of non-45° light. Moreover, in Kishner the diffuser does not compensate for variations in the light output of the lamp.

Other illuminators known in the art also suffer from the ability to use available types of lamps, or lamps of wide-ranging shape. For example, U.S. Pat. No. 4,422,135 to McCamy discloses an annular illuminator with a combination of a spheric mirror, an elliptical mirror, and a circular cylindric mirror to create 45° illumination. McCamy requires that the shape of the lamp that is employed must be that nearly approximating a point source of light, and therefore various lamp shapes or lamp types currently in use may not be employed. Further, the illumination angles created are different for points of the object not on the center axis, so that the ANSI 45°/0° standard is difficult to meet. Finally, with McCamy a suitable reference for correcting lamp variations is difficult to obtain and, therefore, measurements are subject to drift and poor repeatability.

Accordingly, there exists a need for a conical illuminator which uniformly illuminates an object surface at a uniform 45° angle, at all points on the surface, and which compensates for light output variations, and which can employ a variety of lamp types or lamp shapes. Moreover, there exists a need for a conical receiver optical system that provides uniformity in angular and spacial geometry.

SUMMARY OF THE INVENTION

In view of the foregoing, it is an object of the present invention to provide an illuminator or optical receiver for use in colorimetry and spectrophotometry which illuminates or collects light from a measured object and which achieves the applicable industry standard geometric conditions.

It is a further object of the present invention to provide an illuminator for use in colorimetry and reflection spectrophotometry which provides precise conical illumination over the entire surface of the sample plane which may employ a variety of shapes and types of lamp sources.

It is still an object of the present invention to provide an illuminator for use in colorimetry, spectrophotometry, sensitometry or densitometry, which provides precise uniform 45°±5° conical illumination while able to compensate for variations inherent in the light output of the lamp source.

The foregoing specific objects and advantages of the invention are illustrative of those which can be achieved by the present invention and are not intended to be exhaustive or limiting of the possible advantages which can be realized. Thus, those and other objects and advantages of the invention will be apparent from the description herein or can be learned from practicing the invention, both as embodied herein or as modified in view of any variations which may be apparent to those skilled in the art.

Briefly, the invention relates to a conical illuminator for uniform 45° illumination along all points of the sample plane, which may employ a variety of lamp types or shapes, and which compensates for light variation inherent in certain types of lamps, such as pulsed xenon lamps.

In one preferred embodiment, the illuminator includes an integrating chamber coated with a diffuse, highly reflective material (for example, $BaSO_4$). Light introduced into the chamber is optically integrated ("homogenized") and emitted from the chamber through an exit port.

The integrated light is relayed to the object surface by an imaging optic, such as a concave annular reflector or toroidal mirror. An annular stop provides an annular aperture between the integrating chamber exit port and the imaging optic. The annular aperture is telecentric by being placed at or near the tangential focal length of the optic. The stop physically prevents non-conforming rays from reaching the annular reflector, while the annular aperture passes through a substantially uniform 45° cone of illumination at every point on the sample area. The telecentric configuration provides for the optimal use of the full ±5° degree subtended angle of illumination (e.g., 40° to 50°, inclusive) encompassing the limits of the ANSI 45°:0° standard.

Optical fibers or other light detection arrangements may be placed either within the integrating sphere, or external from the sphere via a port or opening, to provide a light intensity signal useful to normalize the reflectance measurement, to thereby provide compensation for variation in the light source.

The diffusely reflected light is measured by a photodetector which detects light normal to the sample surface. To facilitate the measurement of the diffused efflux, a mirror may be placed incident to the normal and above the sample plane. The mirror reflects the near normal diffused light away from the normal to a conveniently located detector. Alternatively, a fiber optic, located along the optical axis of the illuminator, may be employed to collect the diffused light reflected near normal to the sample. The fiber optic conveys the collected light to a convenient location for detection. Other detection schemes are also possible.

The annular stops can be formed from sections of spherical mirrors, or from sections of polished, grooved surfaces. In these embodiments, light is reflected back into the integrating chamber, improving the efficiency and uniformity of the light integration.

It is understood that the configuration (geometry) of the illuminator may also be conformed to other standards of illumination, or as the user desires, the ANSI 45°:0° standard serving only to illustrate the need and the principles of the invention. It is also understood that the geometry control advantageously allows design flexibility. For example, the annular telecentric aperture may be rendered adjustable, to control the subtended angle of the influx, thereby rendering the illuminator capable of achieving multiple geometrical standards. This may be accomplished, for example, through the use of mechanical irises to control the size of the aperture. Similarly, electro-optical shutters, such as a liquid crystal array, may be used to control the degree of aperture. Alternatively, interchangeable forms of the annular stop may be provided to enable the user to selectively control the size of the aperture.

The light source may be located within the integrating chamber, or may be located adjacent the integrating chamber.

BRIEF DESCRIPTION OF THE DRAWINGS

The invention is more particularly described by way of reference to the following drawings, in which.

DETAILED DESCRIPTION OF THE DRAWINGS

Figure 1:
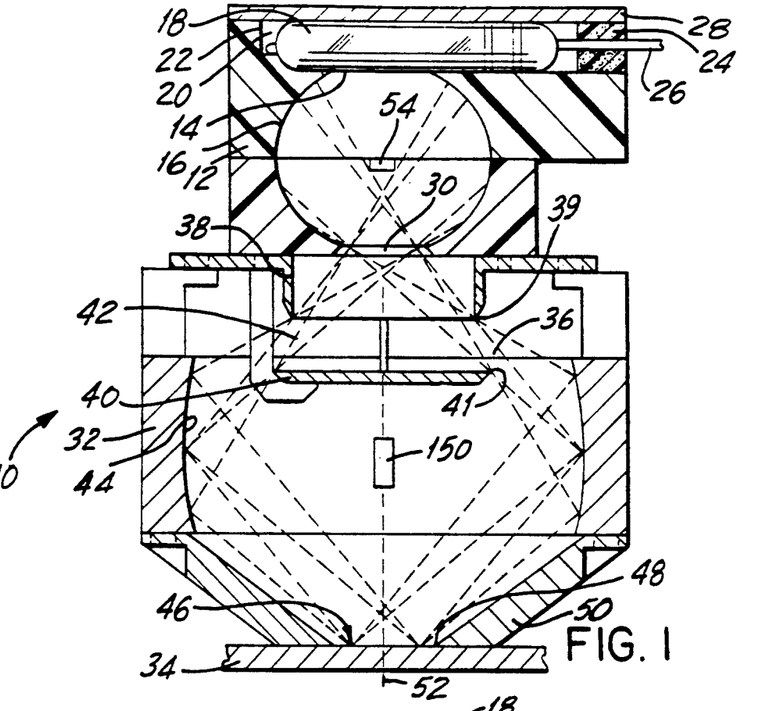
FIG. 1 is a sectional view of one embodiment of a conical illuminator according to the present invention.

Referring now to the drawing figures, in which like numerals refer to like components, there is illustrated in FIG. 1 a preferred embodiment of a conical illuminator 10 according to the invention. The illuminator 10 includes a light integrating chamber 12, for uniformly integrating and homogenizing the light flux introduced into the chamber via an entrance port 14. The chamber 12 also includes an exit port 30 for emitting integrated light. The chamber 12 is preferably spherically shaped. Advantageously, the inner surface 16 of the chamber 12 is diffusive and reflective, which may be accomplished by coating the inner surface 16 with a suitable diffuse and highly reflective coating, such as BaSO$_4$. However, other types of diffusive, reflective coatings, such as powderized polytetrafluorethylene ("PTFE") (registered under the tradename "Halon" by DuPont), magnesium oxide, or various paints, both white or colored, may also be employed. In addition, if the chamber 12 is formed from a material which serves to create a suitably diffusive surface 16, such as ceramic, then no diffusive coating would be necessary.

The light flux introduced into the chamber 12, via entrance port 14, is provided by a lamp 18, such as a pulsed xenon lamp, fixed in a second integrating cavity 20 affixed to the integrating chamber 12. Other lamp types, such as incandescent lamps, arc lamps, gas discharge lamps, lasers, or light emitting diodes ("LEDs") are also employable. For example, different colored LED's may be used depending on the sample color being measured. The second integrating cavity 20 may serve to enhance the integrating effects produced by the integrating chamber 12. The second integrating cavity 20 may also feature an inner surface 22 coated with a diffusive and highly reflective coating, such as BaSO$_4$.

The lamp 18 may be removably inserted into the second integrating cavity 20 via an entrance 24. A cover 28 is removably affixed to the top of the second cavity 20 to provide access thereto. Leads 26 connected to the lamp 18 jut through the entrance 24, so that a source of electrical current may be provided to energize the lamp 18.

Figure 9:
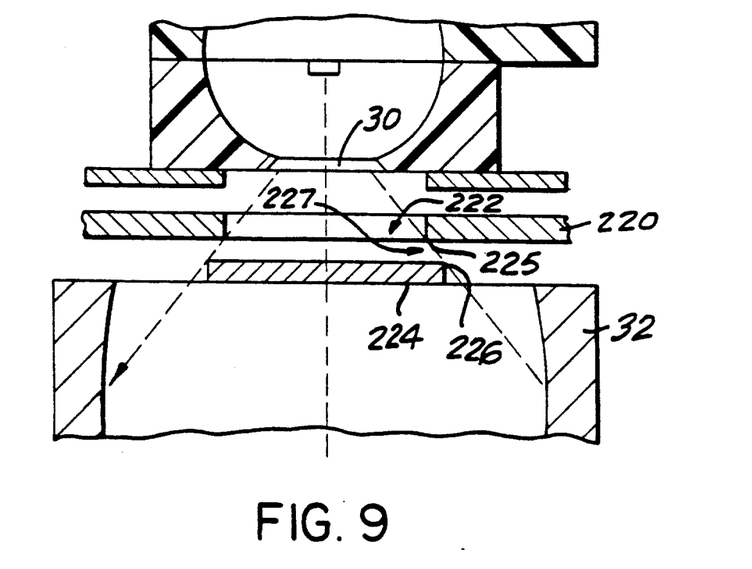
FIG. 9 is a partial sectional view illustrating the general configuration of the annular stop.

An annular stop 36 is placed between the exit port 30 and an imaging optic 32. Referring to FIG. 9, in general the stop 36 includes a first light blocking portion 220 having a rounded opening 222 symmetrically disposed parallel to and about the central axis 52 of the illuminator 10. The first light blocking portion 220 permits only a portion of the light to pass from the exit port 30 through the rounded opening 222, while blocking the rest of the light from passing. The stop 36 further generally includes a rounded second light blocking portion 224 symmetrically disposed perpendicular to and about the central axis 52, for blocking errant, non-conforming light from passing from rounded opening 222 to the imaging optic 32. The free edges 225, 226 of the rounded opening 222 and the second light blocking portion 224 define an annular aperture 227 circumferentially disposed around the annular stop 36 for conforming the light to the prescribed angular standard. The annular aperture 227 is located at or near the tangential focal length of the imaging optic 32, which creates a conical telecentric effect.

Figure 2:
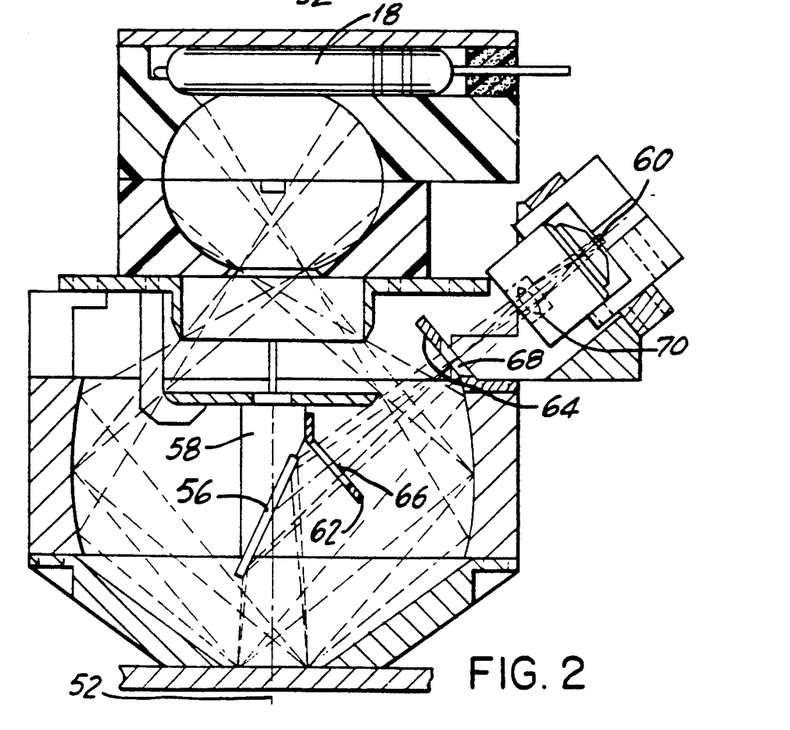
FIG. 2 is a sectional view of the conical illuminator illustrated in FIG. 1 with a reflect light detector added.

As seen in FIGS. 1 and 2, in a preferred embodiment the stop 36 is formed with a hollow, cylindrical portion 38, corresponding to the first light blocking portion 220, that is symmetrically disposed parallel to and about the central axis 52 of the illuminator 10, and is in communication with the exit port 30. The stop 36 also includes a flat, rounded portion 40, corresponding to the second light blocking portion 224, that is placed in communication with cylindrical portion 38 and is symmetrically disposed perpendicular to and about the central axis 52. The edges 39, 41 of the cylindrical portion 38 and horizontal portion 40, respectively, define an annular aperture 42 circumferentially disposed around the annular stop 36. The placement of the annular aperture 42 is chosen at or near the tangential focal length of the imaging optic 32.

As herein illustrated, the surfaces of the cylindrical portion 38 and rounded portion 40 are coated with a non-reflective, light absorbing coating, such as flat black paint. The coating ensures that stray light flux (e.g. light flux not conforming to the applicable standard) will be substantially absorbed without inadvertently reflecting through or otherwise emerging through the aperture 42.

The imaging optic 32 is telecentrically disposed below and around the annular aperture 42. The optic 32 may be formed with a concave annular reflector surface 44. Significantly, the imaging optic 32 contributes to uniform illumination along the sample plane 34, because the optic 32 is capable of relaying the image of exit port 30 to to the sample plane 34 in a telecentric manner. Non-imaging reflective surfaces are incapable of this function.

If the optic 32 is formed from a hard metal, such as steel, aluminum, or copper, a mirrored finish may be imparted to the concave annular reflector surface 44 by polishing. Alternatively, a mirrored finish may be formed by smoothly coating the reflector surface 44 with a suitable reflective material, such as silver.

Figure 7:
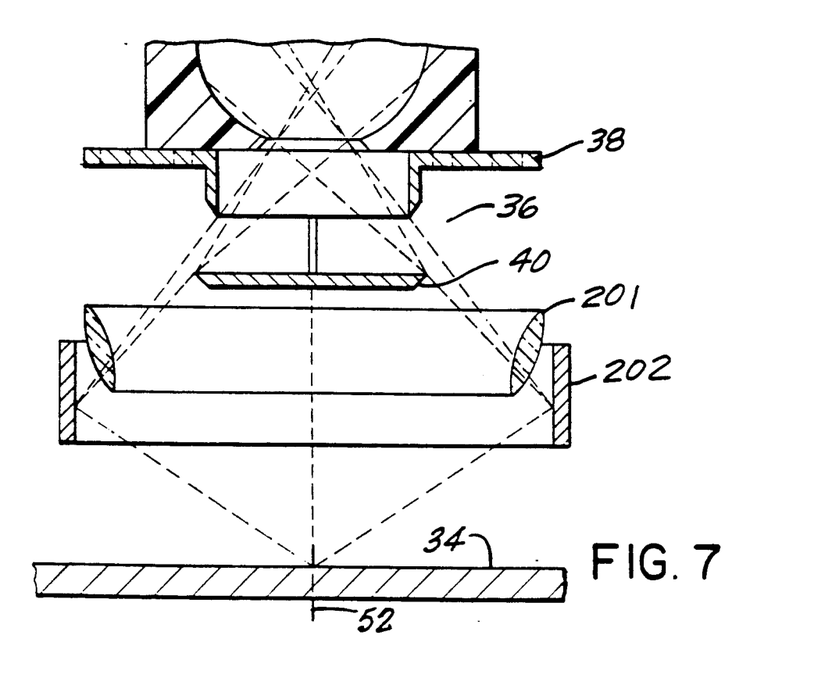
FIG. 7 is a partial sectional view of a variant of the imaging optic.
Figure 8:
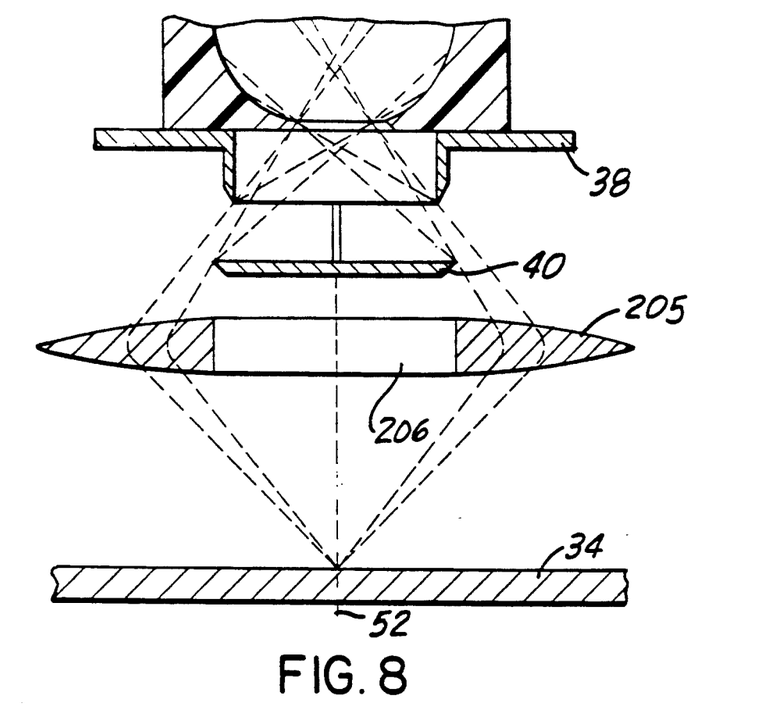
FIG. 8 is a partial sectional view of a further variant of the imaging optic.

The imaging optic 32 may also be formed from a section of a toroidal mirror. Alternatively, the optic 32 may be injection molded, with the concave annular reflector surface 44 coated with a suitable reflective material. In addition, as seen in FIG. 7, the imaging optic 32 may be formed from a convex annular lens 201 symmetrically disposed parallel to and about the central axis 52 of the illuminator 10. The convex annular lens 201 is then disposed within and surrounded by a cylindrical mirror 202. Moreover, as seen in FIG. 8, the imaging optic 32 may be formed from a convex lens 205 whose axis is coaxial with the central axis 52. The lens 205 may have the center 206 bored away for the convenient positioning of light detectors or the like. Other means for producing the imaging optic 32 may be employed by those skilled in the art.

The illuminated portion 46 of the sample plane 34 may be conveniently positioned by a central, flat faced opening 48 in a truncated cone 50. The cone 50, which may be removably affixed to the imaging optic 32, is placed against the sample plane 34. The flat faced opening 48 rests flush against the sample plane 34. It is understood that the sample plane 34 refers either to a planar surface which is to be measured, or to a discrete object or specimen placed upon the plane 34, visible through the opening 48, which is to be measured.

Suitable receptor optics, such as light detectors or optical fibers 150, for relaying light to a suitable external light measurement device, may be located along the normal and along the central axis 52 of the device 10 so as to collect light reflected from the sample.

Advantageously, the entrance port 14 is geometrically located on the integrating chamber 12 such that substantially all the light flux entering from the second integrating cavity 20 may not pass through the integrating chamber 12 and to the sample plane 34 without at least one reflection off of the inner surface 16. The minimal portion of the light which does not bounce off the surface of the chamber 12, i.e., that which directly passes through exit port 30, is either blocked or absorbed by the stop 36. Accordingly, the configuration contributes to enhanced integration and homogenization of the light emitted from the exit port 30. In addition, there is realized a uniform light intensity at the exit port 30, so as to contribute to uniform illumination at all points on the sample plane 34.

The entrance 24 and the cover 28 may be sealed or plugged to prevent light flux from leaking from the second cavity 20, so that substantially all of the light flux is emitted through the entrance port 14 and into the integrating chamber 12. The lamp 18, which is removable, may be changed or replaced, depending on the intended application of or the illuminator 10, the need to replace the lamp, or as the user desires.

As shown in FIG. 1, the light flux introduced into the integrating chamber 12 reflects off of the surface 16 one or more times, so that it is optically integrated and homogenized. The integrated light flux is emitted from the integrating chamber 12 through the exit port 30 for, as will be shortly discussed, optical relay and imaging, via the concave annular reflector surface 44 of the imaging optic 32, to the sample plane 34 to be measured.

Prior to relaying of the optical image of the integrated light flux from exit port 30 to the imaging optic 32, the light influx is conformed to the prescribed 45°:0° standard via the annular aperture 42 of annular stop 36. The placement, geometry and dimensions of the cylindrical portion 38 and of the rounded portion 40 are chosen, with consideration to the size, focal length, magnification, and other parameters associated with the annular reflector surface 44 of imaging optic 32, so that flux exceeding the angular limits prescribed by applicable standard (in the case of the ANSI 45°:0° standard, less than 40° or greater than 50°, measured from the normal of the sample plane 34) will be blocked and not allowed to pass through the annular aperture 42 and onto the annular reflector surface 44.

As can be seen in FIG. 1, this geometry creates a conical telecentric effect, so that the light exiting from the exit port 30 and which passes through the annular aperture 42 is uniformly projected by the concave annular reflector surface 44 in a conical configuration onto each point of the illuminated portion 46 of the sample plane 34. For example, for the geometry chosen to conform the light to the ANSI 45°:0° standard, light passing the edge 39 of the vertical section 38 is projected onto all points of the sample plane 34 in a 40° cone. By contrast, the light passing the edge 41 of the horizontal portion 40 is uniformly projected onto all points of the sample plane 34 in a 50° cone. Light passing at points in the annular aperture 42 between edges 39 and 41 will be projected onto plane 34 at angles between 40° and 50°, with the light that passes directly between edges 39 and 41 reflected at the optimal 45° angle. As known to those skilled in the art, this optimal ray is known as the chief ray or principal ray. Hence, it can be seen that because of the telecentric effect created by placement of the annular aperture 42 at the tangential focal length of the imaging optic 32, i.e., the telecentric geometry of the annular aperture 42 in relation to the imaging optic 32, the uniform 45°:0° cone of illumination is achieved at all points on the illuminated portion 46 of sample plane 34.

As previously described, the geometry of the concave annular reflector surface 44 is telecentrically selected, according to optical principles, so that it cooperates with the placement of the annular stop 36 to reflect the light flux that is emitted through the annular aperture 42 onto all points of the illuminated portion 46 in a uniform angular cone conforming to the applicable standard. For the ANSI 45°:0° standard, the light flux is uniformly reflected onto the illuminated portion 46 in a substantially 45°±5° cone.

The dimensions of the truncated cone 50 are selected so that the light flux reflected off of the imaging optic 32 will be properly imaged, at the applicable standard angle, onto the illuminated portion 46 visible through the opening 48. From the above configuration, light flux which strikes the illuminated portion 46 will be diffused within the interior area defined by the imaging optic 32 and the truncated cone 50. The diffused light will be reflected upwards from a measurement specimen placed against the sample plane 34 and covering the illuminated portion 46.

Advantageously, the illuminator 10 may correct for light variations in the lamp 18. The integrating chamber 12 features one or more port(s) 54 for the insertion of reference fibers or reference detectors within the interior of the chamber 12. Alternatively, light may be collected through the port(s) 54 for detection and measurement at an external location. Because the geometry of the integrating chamber 12 homogenizes and integrates the light, the port(s) 54 provide a very precise sampling area for light variations of the lamp 18, which variations contribute to variations in light intensity at the exit port 30, and thus variations in light intensity at the illuminated area 46. The reference fibers serve to provide a light intensity signal useful to normalize the reflectance measurement. That is, the signal may be relayed to the detector of the light reflected from the sample plane 34 in order to normalize the calculation of that detector. Alternatively, the signal may be used to control light output of the lamp 18.

Light sampling may also occur with the light emitted at the exit port 30, either prior to reaching the annular stop 36, or prior to reaching the sample plane 34. For this purpose, reference fibers or detectors are appropriately disposed within the illuminator 10, in order to implement light sampling as previously described above.

FIG. 2 illustrates a conical illuminator, as previously described, with a reflect light detector added. Here, a mirror 56 is angularly affixed above the illuminated portion 46. The mirror 56, attached to a bracket 58 mounted to the lower portion 40 of the annular stop 36, rests along the central axis 52 of the illuminator 10. In order to prevent stray light not reflected from the sample plane 34 from reaching the reflect detector, baffles 62, 64, having openings 66, 68, may be placed along the path to a light detector or optical fiber 60.

Diffused light reflected from a specimen at the sample plane 34 is reflected off of the mirror 56, and projected towards receiver optics 70 and the detector or optical fiber 60 for measurement. If the baffles 62, 64 are employed, their openings 66, 68 and/or the receiver optics 70 help to insure the passage only of light which conforms to the prescribed diffused efflux cone associated with the applicable standard (for ANSI 45°:0°, light within the 5° cone). The light then passes through the receiver optics 70 prior to being received at the detector 60.

As illustrated, the mirror 56 allows the detector 60 to be conveniently placed outside the illuminator 10, simplifying construction and use of the device. Of course, it is understood that substitutes for mirror 56, such as a prism, may also be used to redirect the light.

Figure 3:
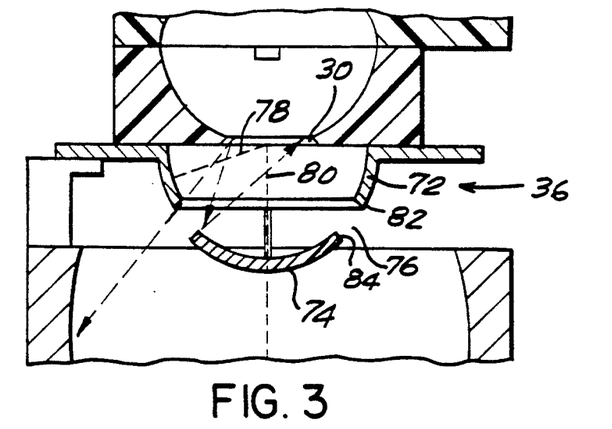
FIG. 3 is a partial sectional view showing a variant of the annular stop.
Figure 4:
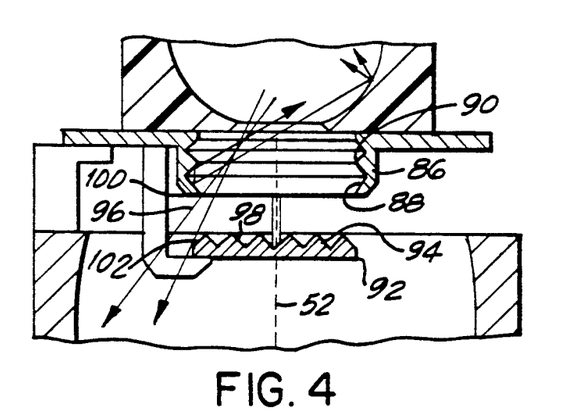
FIG. 4 is a partial sectional view of another variant of the annular stop.

As seen in FIGS. 3 and 4, the annular stop 36 may be formed in alternative manners. FIG. 3 illustrates that the annular stop 36 may be formed as segments of a spherical mirror(s). A tubular first spherical mirror segment 72 is symmetrically aligned parallel to and about the central axis 52 and is in communication with the exit port 30. A rounded spherical mirror segment 74 is placed in communication with mirror segment 72 and is symmetrically aligned perpendicular to and about the central axis 52. The mirror segments 72, 74 define an annular aperture 76 circumferentially disposed around the exit port 30.

The mirror segments 72, 74 are fixed so that their respective centers of curvature 78, 80 are substantially centered in the plane of the exit port 30 and along the central axis 52. Advantageously, the mirror segments 72, 74 may be of the same, or of different, radii of curvature.

As before, the annular aperture 76 is placed at or near the tangential focal length of the imaging optic 32, in order to create the telecentric advantages as previously described. The edges 82, 84 of the mirrors may, advantageously, serve to define the annular aperture 76, similar in function to the edges 39, 41 described in connection with FIG. 1.

In this embodiment, the light emitted from the exit port 30 that does not conform to the prescribed angle of illumination is neither absorbed nor scattered by the annular stop 36. The non-conforming light is reflected off of the mirror segments 72, 74 back through the exit port 30 for re-integration by the integration chamber 12. Light which meets the applicable angular standard of illumination will be allowed to pass through the annular aperture 76 for relay by the imaging optic 32 to the sample plane 34.

Accordingly, light passing through the aperture 76 is shaped by the annular aperture 76 to contribute to a uniform cone illuminating the image surface 34. Placing the centers of curvature 78, 80 at the plane of exit port 30 insures maximal reflection of light into the chamber 12. Thus, the light efficiency of the illuminator 10 is enhanced, thereby allowing use of a lower intensity lamp, or a quicker reading of the sample. Moreover, the uniformity of the light emitted from the exit port 30 is further improved, owing to the additional integration of the light within the integrating chamber 12. This in turn contributes to more accurate light sampling at the port(s) 54.

Although the efficiency of the illuminator is enhanced if both segments 72, 74 are mirrored, it is understood that either one may be formed to have a non-mirrored surface, so that only a portion of the stop 36 is mirrored. The mirrored segment 72 (or 74) would serve to reflect light back through the exit port 30.

FIG. 4 illustrates another variant of the annular stop 36. A hollowed rounded portion, such as a cylinder 86, is symmetrically aligned parallel to and about the central axis 52 and placed in communication with the exit port 30. The cylinder 86 includes a grooved mirrored surface 88, which surface is formed by a plurality of grooves 90 concentric about the central axis 52. As seen in FIG. 4, the grooves 90 are each formed with straight sided walls mutually disposed at a 90° angle, and each groove 90 possesses a 90° apex.

A circular plate 92, having a grooved mirrored surface 94, is placed in communication with the cylinder 86 and is symmetrically aligned perpendicular to and about the central axis 52. The edges 100, 102 of the cylinder 86 and plate 92, respectively, define an annular aperture 96 circumferentially disposed around the exit port 30. A plurality of circular grooves 98 concentric around the central axis 52, also formed with straight sided walls mutually disposed at a 90° angle and each having a 90° apex, form the mirrored surface 94. The annular aperture 96 is also positioned at or near the tangential focal length of the imaging optic 32 to achieve the telecentric advantages previously described.

As with the spherical mirrors 72, 74 of FIG. 3, the mirrored grooved surfaces 88, 94 reflect non-conforming light back through exit port 30 for re-integration by the chamber 12. Significantly, the advantage of a 90° apex is that a two-dimensional retro-reflective condition is created, allowing light to be reflected back onto itself (as seen in FIG. 4). As grooves 90, 98 are concentric about the central axis 52, the reflection is also symmetric about the central axis. Thus, all of the non-conforming light is substantially reflected back into exit port 30. Light conforming to the applicable illumination standard passes through the annular aperture 96 as previously described. Advantageously, the combination of the 90° apex of the grooves 98, 90, producing the retro-reflective condition, coupled with the grooves' concentricity around central axis 52, improves the light efficiency, referencability, and uniformity of the illuminator 10.

As with the mirrored variant of stop 36 illustrated in FIG. 3, it is understood that either one of cylinder 86 or circular plate 92 may be provided with a non-grooved or mirrored surface (ie., a smooth, flat-finished surface), so that only a portion of the stop 36 has a mirrored, grooved surface. The mirrored, grooved surface 88 (or 94) would then serve to retroreflectively reflect light back through exit port 30.

Figure 5:
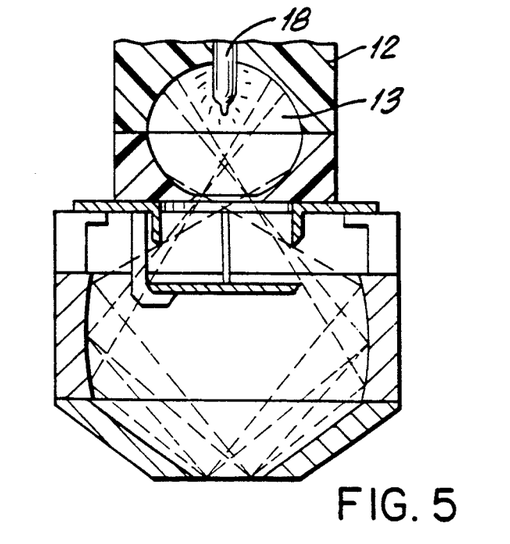
FIG. 5 is a sectional view showing a variant of the integrator/lamp construction.

FIG. 5 illustrates an additional embodiment of the illuminator 10, wherein the lamp 18 is placed directly within the integrating chamber 12, thereby eliminating the second cavity 20.

Figure 6:
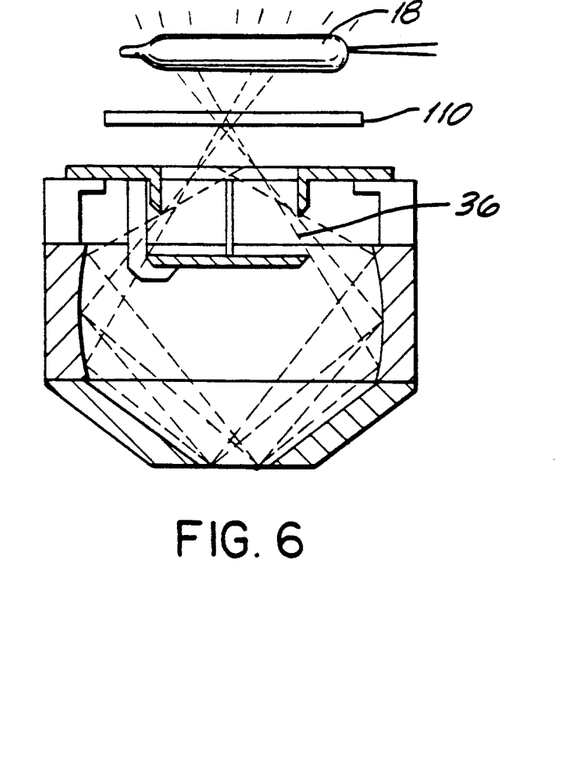
FIG. 6 is a sectional view of a further embodiment according to the invention.

As illustrated in FIG. 6, a further embodiment according to the invention eliminates use of the integrating chamber 12. Here, in lieu of the integrating chamber arrangement, a diffuser 110 is placed in front of annular stop 36. Lamp 18 projects light through diffuser 110, which scatters light through annular aperture 42, for conforming the light influx to the prescribed standard as previously described. The diffuser 110 substitutes for the integrating chamber 12, so as to homogenize and integrate the light prior to passage through stop 36. As before, the modified annular stops 36, shown in FIGS. 3 4, and the modified imaging optics 32, illustrated in FIGS. 7 and 8, may be employed.

It will be apparemt that other and further forms of the invention may be devised without departing from the spirit and scope of the appended claims, it being understood that this invention is not limited to the specific embodiments shown.

We claim:

1. A conical illuminator, comprising:
   a source of light;
   means for homogenizing the light;
   an annular stop for geometrically conforming said light to a pre-selected standard;
   an imaging optic for relaying said conformed light to a sample plane, said annular stop located at or near the tangential focal length of said imaging optic, and;
   means for establishing spacing from said imaging optic to said sample plane.

2. A conical illuminator, comprising:
   a source of light;

an integrating chamber for homogenizing said light;
an annular stop for geometrically conforming said light to a pre-selected standard;
an imaging optic for relaying said conformed light to a sample plane, said annular stop located at or near the tangential focal length of said imaging optic, and;
means for establishing spacing from said imaging optic to said sample plane.

3. The conical illuminator of claim 2, further comprising means for detecting light diffused from the surface of said sample plane.

4. The conical illuminator of claim 3, wherein said light detecting means further comprises a mirror disposed along the central axis of said illuminator and above said sample plane for deflecting said diffused light towards said light detecting means.

5. A conical illuminator comprising:
lamp means for emitting light;
an integrating chamber having a diffuse reflective surface for integrating the light introduced into said chamber, said chamber having an exit port for releasing the integrated light;
an annular stop for geometrically conforming the integrated light that is released from said exit port into a conical configuration defined by pre-selected standards;
an imaging optic for relaying said geometrically conformed light uniformly onto a sample plane, wherein said annular stop is placed at or near the tangential focal length of the imaging optic; and
means for establishing spacing from said imaging optic to said sample plane.

6. The conical illuminator of claim 5, further comprising means for detecting light diffused from the surface of said sample plane.

7. The conical illuminator of claim 5, wherein said annular stop comprises:
a first light blocking portion in communication with said exit port and defining a rounded opening symmetrically disposed parallel to and about the central axis of said illuminator, said rounded opening having a free edge portion;
a second rounded light blocking portion in communication with said first light blocking portion and symmetrically disposed perpendicular to and about the central axis of said illuminator, said second rounded light blocking portion having a free edge portion,
wherein the free edge portions of said rounded opening and said second rounded light blocking portion define an open gap constituting said annular aperture.

8. The conical illuminator of claim 7, wherein said first and second light blocking portions are coated with a light absorbing coating.

9. The conical illuminator of claim 5, wherein said imaging optic comprises a concave annular reflector surface.

10. The conical illuminator of claim 5, wherein said optic comprises:
a convex annular lens symmetrically disposed parallel to the central axis of said illuminator; and
a cylindrical mirrored surface symmetrically disposed about said convex annular lens.

11. The conical illuminator of claim 5, wherein said imaging optic comprises a convex lens symmetrically disposed perpendicular to the central axis of said illuminator, wherein the axis of said convex lens is coaxial with the central axis of the illuminator.

12. The conical illuminator of claim 5, wherein said lamp means is disposed within said integrating chamber.

13. A conical illuminator comprising:
lamp means for emitting light;
an integrating chamber having a diffuse reflective surface for integrating the light introduced into said chamber, said chamber having an exit port for releasing the integrated light;
an annular stop for geometrically conforming the integrated light that is released from said exit port into a conical configuration defined by pre-selected standards, comprising a first light blocking portion in communication with said exit port and defining a rounded opening symmetrically disposed parallel to and about the central axis of said illuminator, said rounded opening having a free edge portion, said annular stop further comprising a second rounded light blocking portion in communication with said first light blocking portion and symmetrically disposed perpendicular to and about the central axis of said illuminator, said second rounded light blocking portion having a free edge portion,
wherein the free edge portions of said rounded opening and second rounded light blocking portion define an open gap constituting said annular aperture,
wherein said first light blocking portion comprises a hollow cylinder, and said second light blocking portion comprises a round plate;
an imaging optic for relaying said geometrically conformed light uniformly onto a sample plane, wherein said annular stop is placed at or near the tangential focal length of the imaging optic; and
means for establishing spacing from said imaging optic to said sample plane.

14. A conical illuminator comprising:
lamp means for emitting light;
an integrating chamber having a diffuse reflective surface for integrating the light introduced into said chamber, said chamber having an exit port for releasing the integrated light;
an annular stop for geometrically conforming the integrated light that is released from said exit port into a conical configuration defined by pre-selected standards, comprising a first light blocking portion in communication with said exit port and defining a rounded opening symmetrically disposed parallel to and about the central axis of said illuminator, said rounded opening having a free edge portion said annular stop further comprising a second rounded light blocking portion in communication with said first light blocking portion and symmetrically disposed perpendicular to and about the central axis of said illuminator, said second rounded light blocking portion having a free edge portion,
wherein the free edge portions of said rounded opening and second rounded light blocking portion define an open gap constituting said annular aperture,
wherein said first light blocking portion comprises an annular spheroidal mirror section having a center of curvature at or near the plane of the exit port, and said second light blocking portion comprises a rounded spheroidal mirror section having a center of curvature at or near the center of the plane of the exit port;

an imaging optic for relaying said geometrically conformed light uniformly onto a sample plane, wherein said annular stop is placed at or near the tangential focal length of the imaging optic; and means for establishing spacing from said imaging optic to said sample plane.

15. A conical illuminator comprising:

lamp means for emitting light;

an integrating chamber having a diffuse reflective surface for integrating the light introduced into said chamber, said chamber having an exit port for releasing the integrated light;

an annular stop for geometrically conforming the integrated light that is released from said exit port into a conical configuration defined by pre-selected standards, comprising a first light blocking portion in communication with said exit port and defining a rounded opening symmetrically disposed parallel to and about the central axis of said illuminator, said rounded opening having a free edge portion, and a second rounded light blocking portion in communication with said first light blocking portion and symmetrically disposed perpendicular to and about the central axis of said illuminator, said second rounded light blocking portion having a free edge portion, wherein the free edge portions of said rounded opening and second rounded light blocking portion define an open gap constituting said annular aperture, wherein said first light blocking portion comprises a hollowed rounded portion having an interior surface with a plurality of mirrored grooves formed thereon, said grooves concentric about the central axis of the illuminator, and wherein said second light blocking portion comprises a rounded plate having a surface with a plurality of mirrored grooves formed thereon, said grooves concentric about the central axis of the illuminator;

an imaging optic for relaying said geometrically conformed light uniformly onto a sample plane, wherein said annular stop is placed at or near the tangential focal length of the imaging optic; and means for establishing spacing from said imaging optic to said sample plane.

16. A conical illuminator comprising:

a first integrating chamber having a diffuse reflective surface, for integrating light introduced into said chamber, the chamber having an exit port and entrance port;

a second integrating chamber having an opening in sealed communication with said entrance port and having a diffuse reflective surface for integrating light;

lamp means disposed within the second integrating chamber for emitting light through the entrance port;

an annular stop for geometrically conforming the integrated light that is released through the exit port into a conical configuration defined by a pre-selected standard;

an imaging optic having a tangential focal length and disposed between the annular stop and the sample plane, for relaying the geometrically conformed light uniformly across the sample plane, wherein the annular stop is placed at or near the tangential focal length of the imaging optic; and means for establishing spacing from said imaging optic to said sample plane.

17. The conical illuminator of claim 16, further comprising measurement means for measuring light diffused off of said sample plane.

18. The conical illuminator of claim 16, wherein the imaging optic comprises a concave annular reflector surface.

19. The conical illuminator of claim 16, wherein the imaging optic comprises:

a convex annular lens symmetrically disposed parallel to and about the central axis of said illuminator, and;

a cylindrical mirrored surface symmetrically disposed about said convex annular lens.

20. The conical illuminator of claim 16, wherein the imaging optic comprises a convex lens symmetrically disposed perpendicular to and about the central axis of said illuminator, wherein the axis of said convex lens is coaxial with the central axis of the illuminator.

21. The conical illuminator of claim 17, further comprising means for directing the light diffused from the surface of the sample plane towards the measurement means.

22. The conical illuminator of claim 21, wherein said light direction means comprises a mirror angularly fixed above the surface of the sample plane for directing diffused light along a path away from said sample plane and towards said measurement means.

23. The conical illuminator of claim 16, further comprising one or more light reference detector for monitoring the integrated light.

24. The conical illuminator of claim 23, further comprising measurement means for measuring light diffused off of said sample plane, wherein the light reference detector is coupled to the measurement means and relays signals responsive to said monitoring for controlling the accuracy of the measurement means.

25. The conical illuminator of claim 16, wherein the annular stop comprises:

a first blocking portion in communication with said exit port and defining a rounded opening symmetrically disposed parallel to and about the central axis of said illuminator, said rounded opening having a free edge portion;

a second rounded light blocking portion in communication with said first light blocking portion and symmetrically disposed perpendicular to and about the central axis of said illuminator, said second rounded light blocking portion having a free edge portion, wherein the free edge portions of said rounded opening and said second rounded light blocking portion define an open gap constituting said annular aperture.

26. The conical illuminator of claim 25, wherein said first light blocking portion comprises a hollow cylinder, and said second light blocking portion comprises a rounded plate.

27. The conical illuminator of claim 25, wherein said first and second light blocking portions are coated with a light absorbing coating.

28. The conical illuminator of claim 25, wherein said first light blocking portion comprises an annular spheroidal mirror section having a center of curvature at or near the center of the plane of the exit port, and said second light blocking portion comprises a rounded spheroidal mirror having a center of curvature at or near the center of the plane of the exit port.

29. The conical illuminator of claim 25, wherein said first light blocking portion has a mirrored surface.

30. The conical illuminator of claim 25, wherein said second light blocking portion has a mirrored surface.

31. The conical illuminator of claim 25, wherein said first light blocking portion comprises a hollow rounded portion having an interior surface with a plurality of mirrored grooves formed thereon, said grooves concentric about the central axis of the illuminator, and said second light blocking portion comprises a rounded plate having a surface with a plurality of mirrored grooves formed thereon, said mirrored grooves concentric about the central axis of the illuminator.

32. The conical illuminator of claim 31, wherein the mirrored grooves on the surfaces of the hollow rounded portion and/or rounded plate are formed with a 90° apex.

33. The conical illuminator of claim 25, wherein said first light blocking portion has an interior surface with a plurality of mirrored grooves formed thereon.

34. The conical illuminator of claim 25, wherein said second light blocking portion has a surface with a plurality of mirrored grooves formed thereon.

35. A conical illuminator comprising:
lamp means for emitting light;
a diffuser for homogenizing said light;
an annular stop for geometrically conforming said light to a pre-selected standard;
an imaging optic for relaying said conformed light to a sample plane, said annular stop located at or near the tangential focal length of said imaging optic; and
means for establishing spacing from said imaging optic to said sample plane.

36. A method for conforming light into a standardized conical configuration and relaying the conformed light onto a sample plane, comprising the step of:
homogenizing the light;
passing the homogenized light to an annular stop the annular stop having an annular aperture for shaping the light into a standardized conical configuration while blocking errant light from passing through the aperture;
passing the conically shaped light through the annular aperture and onto an imaging optic, wherein the annular aperture is disposed at the tangential focal length of the imaging optic; and
reflecting the conically shaped light off of the imaging optic onto the sample plane at angles of incidence conforming to the standardized configuration.

37. The method of claim 36, further including the step of directing light diffused from the sample plane towards light measurement means.

38. The method of claim 36, further including the step of coating the annular stop with a light absorbing coating.

39. The method of claim 36, wherein the step of homogenizing the light includes the step of introducing the light into an integrating chamber.

40. The method of claim 36, wherein the step of homogenizing the light includes the step of introducing the light through a diffuser.

41. A method for conforming light into a standardized conical configuration and relaying the conformed light onto a sample plane, comprising the steps of:
homogenizing the light;
passing the homogenized light to an annular stop the annular stop having an annular aperture for shaping the light into a standardized conical configuration while blocking errant light from passing through the aperture;
passing the conically shaped light through the annular aperture and onto an imaging optic, wherein the annular aperture is disposed at or near the tangential focal length of the imaging optic; and
reflecting the conically shaped light off the imaging optic onto the sample plane at angles of incidence conforming to the standardized configuration,
further comprising the step of providing a mirrored spherical surface on the annular stop.

42. A method for conforming light into a standardized conical configuration and relaying the conformed light onto a sample plane, comprising the steps of:
homogenizing the light;
passing the homogenized light to an annular stop, the annular stop having an annular aperture for shaping the light into a standardized conical configuration while blocking errant light from passing through the aperture;
passing the conically shaped light through the annular aperture and onto an imaging optic, wherein the annular aperture is disposed at or near the tangential focal length of the imaging optic; and
reflecting the conically shaped light off the imaging optic onto the sample plane at angles of incidence conforming to the standardized configuration,
further comprising the step of providing a mirrored spherical surface on a portion of an annular stop.

43. A method for conforming light into a standardized conical configuration and relaying the conformed light onto a sample plane, comprising the steps of:
homogenizing the light;
passing the homogenized light to an annular stop the annular stop having an annular aperture for shaping the light into a standardized conical configuration while blocking errant light from passing through the aperture;
passing the conically shaped light through the annular aperture and onto an imaging optic, wherein the annular aperture is disposed at or near the tangential focal length of the imaging optic; and
reflecting the conically shaped light off the imaging optic onto the sample plane at angles of incidence conforming to the standardized configuration,
further comprising the step of grooving the surface of the annular stop with mirrored grooves concentric about the central axis of the illuminator.

44. A method for conforming light into a standardized conical configuration and relaying the conformed light onto a sample plane, comprising the steps of:
homogenizing the light;
passing the homogenized light to an annular stop, the annular stop having an annular aperture for shaping the light into a standardized conical configuration while blocking errant light from passing through the aperture;
passing the conically shaped light through the annular aperture and onto an imaging optic, wherein the annular aperture is disposed at or near the tangential focal length of the imaging optic; and
reflecting the conically shaped light off the imaging optic onto the sample plane at angles of incidence conforming to the standardized configuration,
further comprising the step of grooving a portion of the surface of the annular stop with mirrored grooves concentric about the central axis of the illuminator.

* * * * *